United States Patent
Gu et al.

(10) Patent No.: US 8,214,028 B2
(45) Date of Patent: Jul. 3, 2012

(54) ELECTROCARDIOGRAM ANALYSIS AND PARAMETER ESTIMATION

(75) Inventors: Zhijun Gu, Shanghai (CN); Nanxiong Zhang, Shanghai (CN); Shie Qian, Irvine, CA (US)

(73) Assignee: National Instruments Corporation, Austin, TX (US)

( * ) Notice: Subject to any disclaimer, the term of this patent is extended or adjusted under 35 U.S.C. 154(b) by 346 days.

(21) Appl. No.: 12/699,184

(22) Filed: Feb. 3, 2010

(65) Prior Publication Data

US 2011/0190648 A1 Aug. 4, 2011

(51) Int. Cl.
*A61B 5/0456* (2006.01)
(52) U.S. Cl. ........................ 600/521; 600/509
(58) Field of Classification Search .................. None
See application file for complete search history.

(56) References Cited

U.S. PATENT DOCUMENTS

| 4,680,708 A * | 7/1987 | Ambos et al. ............ 600/509 |
| 2005/0027202 A1* | 2/2005 | Ginzburg et al. .......... 600/509 |
| 2006/0100534 A1* | 5/2006 | Colombo et al. ........... 600/513 |

OTHER PUBLICATIONS

Bert-Uwe Köhler, Carsten Hennig, Reinhold Orglmeister, "The Principles of Software QRS Detection: Reviewing and Comparing Algorithms for Detecting this Important ECG Waveform," IEEE Engineering in Medicine and Biology, Jan./Feb. 2002, pp. 42-57.
Jiapu Pan and Willis J. Tompkins, "A Real-Time QRS Detection Algorithm," IEEE Transactions on Biomedical Engineering, vol. BME-32, No. 3, Mar. 1985, pp. 230-236.
Yun-Chi Yeh and Wen-June Wang, "QRS complexes detection for ECG signal: The Difference Operation Method," Computer Methods and Programs in Biomedicine, 91, 2008, pp. 245-254.
Cuiwei Li, Chongxun Zheng, and Changfeng Tai, "Detection of ECG Characteristic Points Using Wavelet Transforms," IEEE Transactions on Biomedical Engineering, vol. 42, No. 1, Jan. 1995, pp. 21-28.
P. Jafari Moghadam Fard, M.H. Moradi, and M.R. Tajvidi, "A novel approach in R peak detection using Hybrid Complex Wavelet (HCW)," International Journal of Cardiology, 124 (2008), pp. 250-253.
S. Parvaneh and M. Pashna, "Electrocardiogram Synthesis Using a Gaussian Combination Model (GCM)," Computers in Cardiology: 34, 2007, pp. 621-624.
Remi Dubois, et al., "Automatic ECG wave extraction in long-term recordings using Gaussian mesa function models and nonlinear probability estimators," Computer Methods and Programs in Biomedicine: 88 (2007), pp. 217-233.

(Continued)

*Primary Examiner* — Kennedy Schaetzle
(74) *Attorney, Agent, or Firm* — Meyertons Hood Kivlin Kowert & Goetzel, P.C.; Jeffrey C. Hood; Mark K. Brightwell

(57) ABSTRACT

A system, method and memory medium for operating on an electrocardiogram (ECG) signal. A multiscale short-time Fourier transform (STFT) is performed on a set of ECG samples $\{s(n)\}$ to obtain a transform array. For each sufficiently energetic peak in the transform array, a refined window width value and a refined window displacement value is generated by: computing an inner product between the set of samples and each of a plurality of functions, where the plurality of functions are sufficiently close to a coarse approximation function given by the peak location; and solving a linear system $Av=c$ for the unknown vector $v$, where the vector $c$ is determined by the inner products, where the matrix $A$ is determined by the center times of the plurality of functions. After appropriate selection, the refined window width and refined window displacement may be used to represent ECG waveform features.

22 Claims, 11 Drawing Sheets

OTHER PUBLICATIONS

Seth Suppappola, et al., "Gaussian Pulse Decomposition: An Intuitive Model of Electrocardiogram Waveforms," Annals of Biomedical Engineering, vol. 25, 1997, pp. 252-260.

Federica Censi, et al., "P-Wave Morphology Assessment by a Gaussian Functions-Based Model in Atrial Fibrillation Patients," IEEE Transactions on Biomedical Engineering, vol. 54, No. 4, Apr. 2007, pp. 663-672.

Ary L. Goldberger, et al., "PhysioBank, PhysioToolkit, and PhysioNet: Components of a New Research Resource for Complex Physiologic Signals," Circulation: Journal of the American Heart Association, 2000, 7 pages.

Electrocardiography, Wikipedia, the free encyclopedia, http://en.wikipedia.org/wiki/Electrocardiography, 13 pages. [Retrieved Oct. 6, 2009].

Shie Qian, "Introduction to Time-Frequency and Wavelet Transforms," Prentice Hall PTR, 2001, pp. 223-248.

Shie Qian, Dapang Chen, "Joint Time Frequency Analysis and Applications," Prentice Hall, 1996, pp. 46-52 and 190-193.

* cited by examiner

310   Receive Input Signal Block {s(n)}.
315
320   For ( i=0; i<N_web; i++) {
325     For (j=0; j<N_τ; j++) {
330       For (n=0; n<N_S; n++) {
335         y(n) = s(n) w( α(i)^{1/2} ( n-τ(j) ) );
340       }
345       S[i,j,k] = FFT(y(n));
350     }
355   }
360
365   Search over (i, j, k) space for the $N_P$ largest peaks of $|S(i,j,\omega)|$

FIG. 3

ELECTROCARDIOGRAM ANALYSIS AND PARAMETER ESTIMATION

FIELD OF THE INVENTION

The present invention relates to the field of signal processing, and more particularly, to a system and method for detecting QRS complexes within electrocardiogram (ECG) signals.

DESCRIPTION OF THE RELATED ART

An electrocardiogram (ECG) provides information about an individual's cardiac health. An ECG is commonly used in clinical applications to help medical personnel diagnose cardiac diseases. Among the features present in the ECG signal (e.g., features such as the P wave, the T wave, QRS complex, etc.), the QRS complex is very significant because other points in the ECG signal are often measured relative to the QRS onset, the R peak and the QRS offset. During the past several decades, various methods have been proposed for the detection of the QRS complexes from contaminated ECG signals. However, most of these methods require a large computation load. Thus, there exists a need for computationally efficient methods for detecting the QRS complex.

SUMMARY

In one set of embodiments, a method for operating on an electrocardiogram (ECG) signal may include the following processing operations.

A computer system may perform a multiscale short-time Fourier transform (STFT) on a set of samples {s(n)} to obtain a transform array that is parameterized by window width, window displacement $\tau$ and frequency $\omega$. The set of samples may represent a portion of an electrocardiogram (ECG) signal. The signal portion may include a number of waveform features.

The computer system then may operate on the transform array to determine a plurality of peaks in the transform array. The action of operating on the transform array may include determining, for each of the plurality of peaks, a window width value, a window displacement value, a frequency value and a power value.

The computer system may generate, for each of the plurality of peaks, a refined window width value and a refined window displacement value, by: computing an inner product between the set of samples and each of a plurality of functions, where the plurality of functions are windowed sinusoids (a) having a common frequency equal to the frequency value of the peak, (b) being centered at times that are in a neighborhood of the window displacement value of the peak, and (c) having a common width that is based on the width value of the peak; and solving a linear system Av=c for the unknown vector v, where the vector c is determined by the inner products, where the matrix A is determined by the times that are in the neighborhood of the window displacement value of the peak. In one embodiment, the functions are Gaussian-modulated complex exponentials.

In some embodiments, the computer system may also: (d) identify one of the peaks as corresponding to a QRS complex based on a determination that the power value of the peak exceeds a threshold value and that the refined window displacement value for the peak satisfies one or more time constraints; (e) compute a QRS onset time and/or a QRS offset time based on the refined window displacement value and the refined window width of the first peak; and (f) display the QRS onset time and/or the QRS offset time via a display device. The threshold value may be an adaptive threshold that changes over time. The one or more time constraints may include a time constraint on the refined window displacement value of the first peak relative to a time of a previously identified feature in the ECG signal.

In some embodiments, the computer system may also: compute, for each peak $P_j$ of the plurality of peaks, a windowed sinusoid function $h_j$ that is determined by the refined window width value of the peak $P_j$, the refined window displacement value of the peak $P_j$, and the frequency value of the peak $P_j$; generate a linear combination of the windowed sinusoid functions $h_j$; and display the real part of the linear combination via a display device.

The ECG signal may derive from any of a variety of species of organism. For example, in one embodiment, the ECG signal is a human ECG signal, and the waveform features include one or more of the following: a P wave, a QRS complex and a T wave.

In some embodiments, the action of operating on the transform array may include searching for the $N_P$ peaks (or local maxima) of largest absolute value in the transform array, where $N_P$ is a positive integer. In one embodiment, the action of searching for $N_P$ peaks is restricted to a band of frequencies that is smaller than the frequency range of the multiscale STFT.

In another set of embodiments, a method for operating on an ECG signal may include the following operations.

A computer system may receive samples of a portion of an electrocardiogram (ECG) signal, where the signal portion contains a waveform feature.

The computer system may operate on the samples to compute a plurality of short-time Fourier transforms (STFT), where each of the STFTs is computed using a different value of window width, where each of the STFTs is a function of window displacement time $\tau$ and frequency $\omega$.

The computer system may search the plurality of STFTs to determine an initial set of parameters values that characterize the waveform feature, where the initial set of parameter values includes a first window displacement time $\tau_0$, a first frequency $\omega_0$ and a first window width $\sigma_0$.

The computer system may compute an inner product of the samples with each of a first function, a second function and a third function to obtain respectively a first complex value, a second complex value and a third complex value. The first, second and third functions may be windowed sinusoids (a) having a common frequency equal to the first frequency $\omega_0$, (b) being centered at times that are in a neighborhood of the first window displacement time $\tau_0$, and (c) having a common width that is based on the first window width $\sigma_0$.

The computer system may compute a time of the waveform feature and a duration of the waveform feature based on the first, second and third complex values and based on the times in the neighborhood of the first window displacement time $\tau_0$.

The computer system may store the waveform feature time and the waveform feature duration in a memory.

In some embodiments, the computer system may display the waveform feature time or a visual indication of the waveform feature time via a display device.

In some embodiments, the computer system may compute an onset time and/or an offset time of the QRS complex based on the waveform feature time and the waveform feature duration. The onset time and/or the offset time may be display via the display device.

The waveform feature may be a feature such as the QRS complex or the T wave or the P wave of a human ECG signal.

The plurality of STFTs may be computed using Gaussian windows. Although, a wide variety of other types of windows may be used.

The windowed sinusoids may be Gaussian-modulated complex exponentials, although other types of windowed sinusoids may be used.

In some embodiments, the action of searching the plurality of STFTs may include searching for a local maximum or global maximum of absolute value in the STFTs.

In some embodiments, the action of searching the plurality of STFTs may be restricted to frequencies in a predetermined frequency interval, e.g., the interval from 10 Hz to 25 Hz.

In some embodiments, the action of computing the waveform feature time and the waveform feature duration includes solving a linear system $Av=c$ for the unknown vector $v$, where the matrix $A$ is determined by the times in the neighborhood of the first window displacement time $\tau_0$, where the vector $c$ is determined by the first, second and third complex values. In one embodiment, the vector $c$ is determined by the expression:

$$c=[\ln|z_0|/|z_{-1}|, \ln|z_0|/|z_{+1}|]^T,$$

where "ln" denotes the natural logarithm, where the superscript "T" denotes the transpose operator, where $z_0$, $z_{-1}$ and $z_{+1}$ are the first, second and third complex values, respectively.

In some embodiments, the times that are in the neighborhood of the first window displacement time $\tau_0$ include $\tau_0$, $\tau_0+\Delta\tau$ and $\tau_0-\Delta\tau$, where $\Delta\tau$ is a positive real number.

BRIEF DESCRIPTION OF THE DRAWINGS

A better understanding of the present invention can be obtained when the following detailed description of the preferred embodiments is considered in conjunction with the following drawings.

FIG. 3 shows one embodiment of a method for performing a coarse search for features in an ECG signal.

Figure 1:
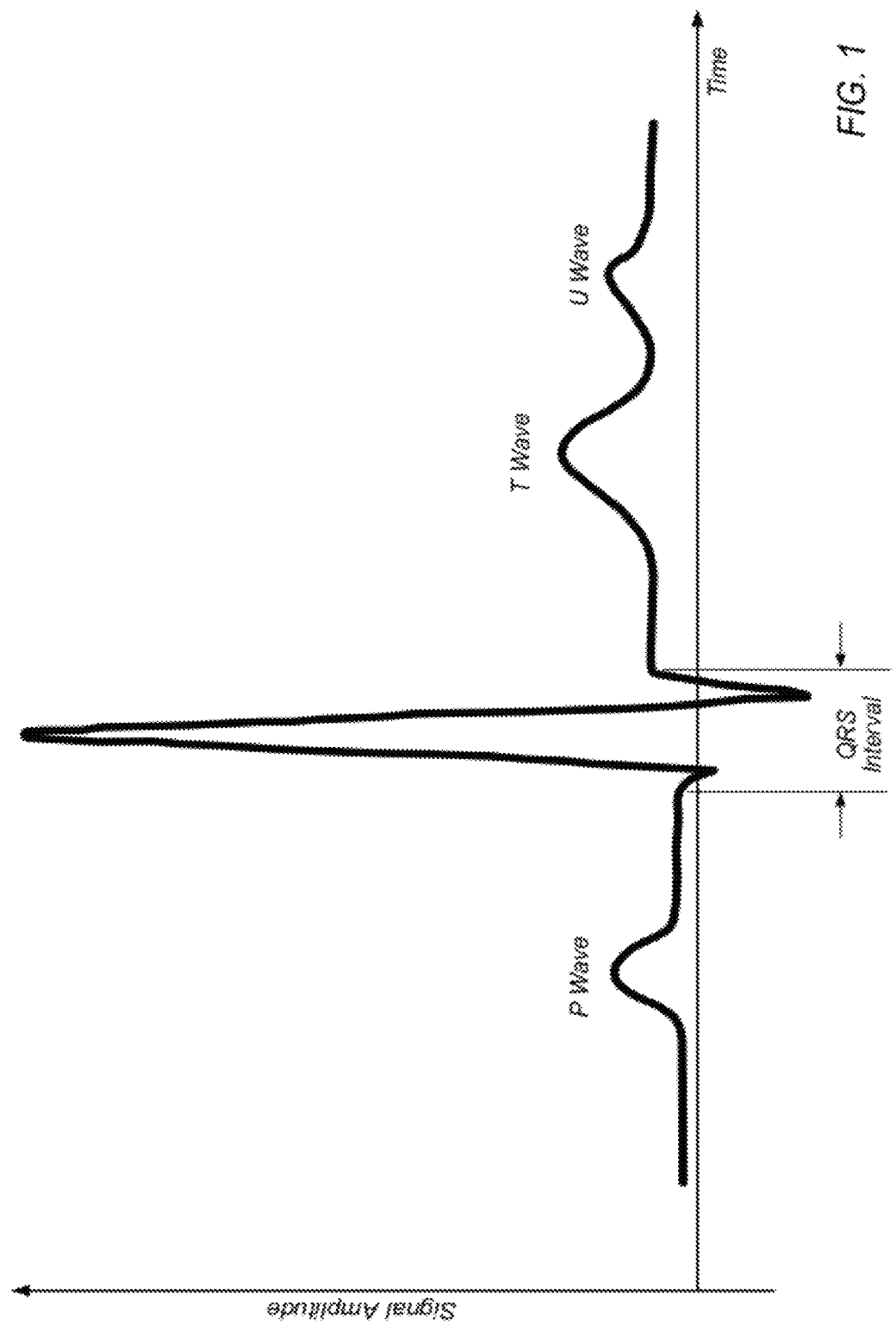
FIG. 1 shows one cycle of a typical ECG signal.

While the invention is susceptible to various modifications and alternative forms, specific embodiments thereof are shown by way of example in the drawings and are herein described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

Terminology

The following is a glossary of terms used in the present document.

Memory Medium—A memory medium is a medium configured for the storage and retrieval of information. Examples of memory media include: various kinds of semiconductor memory such as RAM and ROM; various kinds of magnetic media such as magnetic disk, tape, strip and film; various kinds of optical media such as CD-ROM and DVD-ROM; various media based on the storage of electrical charge and/or other physical quantities; media fabricated using various lithographic techniques; etc. The term "memory medium" may also include a set of two or more memory media which reside at different locations, e.g., at different computers that are connected over a network.

Programmable Hardware Element—includes various hardware devices comprising multiple programmable function blocks connected via a programmable interconnect. Examples include FPGAs (Field Programmable Gate Arrays), PLDs (Programmable Logic Devices), FPOAs (Field Programmable Object Arrays), and CPLDs (Complex PLDs). The programmable function blocks may range from fine grained (combinatorial logic or look up tables) to coarse grained (arithmetic logic units or processor cores). A programmable hardware element may also be referred to as "reconfigurable logic".

Program—the term "program" is intended to have the full breadth of its ordinary meaning As used herein, the term "program" means: 1) a software program which may be stored in a memory and is executable by a processor, or, 2) a hardware configuration program useable for configuring a programmable hardware element. Any of the method embodiments described herein, or, any combination of the method embodiments described herein, or, any subset of any of the method embodiments described herein, or, any combination of such subsets may be implemented in terms of one or more programs.

Software Program—the term "software program" is intended to have the full breadth of its ordinary meaning, and includes any type of program instructions, code, script and/or data, or combinations thereof, that may be stored in a memory medium and executed by a processor. Exemplary software programs include: programs written in text-based programming languages such as C, C++, Java™, Pascal, Fortran, etc.; graphical programs (programs written in graphical programming languages); assembly language programs; programs that have been compiled to machine language; scripts; and other types of executable software. A software program may comprise two or more subprograms that interoperate in some manner.

Hardware Configuration Program—a program, e.g., a netlist or bit file, that can be used to program or configure a programmable hardware element.

Graphical Program—A program comprising a plurality of interconnected nodes or icons, where the plurality of interconnected nodes or icons visually indicate functionality of the program. A graphical program is a type of diagram.

The following provides examples of various aspects of graphical programs. The following examples and discussion are not intended to limit the above definition of graphical program, but rather provide examples of what the term "graphical program" encompasses.

The nodes in a graphical program may be connected in one or more of a data flow, control flow, and/or execution flow format. The nodes may also be connected in a "signal flow" format, which is a subset of data flow.

Exemplary graphical program development environments which may be used to create graphical programs include LabVIEW, DasyLab, DiaDem and Matrixx/SystemBuild from National Instruments, Simulink from the MathWorks, VEE from Agilent, WiT from Coreco, Vision Program Manager from PPT Vision, SoftWIRE from Measurement Computing, Sanscript from Northwoods Software, Khoros from Khoral Research, SnapMaster from HEM Data, VisSim from Visual Solutions, ObjectBench by SES (Scientific and Engineering Software), and VisiDAQ from Advantech, among others.

The term "graphical program" includes models or block diagrams created in graphical modeling environments, where the model or block diagram comprises interconnected nodes or icons that visually indicate operation of the model or block diagram; exemplary graphical modeling environments include Simulink, SystemBuild, VisSim, Hypersignal Block Diagram, etc.

A graphical program may be represented in the memory of the computer system as data structures and/or program instructions. The graphical program, e.g., these data structures and/or program instructions, may be compiled or interpreted to produce machine language that accomplishes the desired method or process as shown in the graphical program.

Input data to a graphical program may be received from any of various sources, such as from a device, a unit under test, a process being measured or controlled, another computer program, a database, or from a file. Also, a user may input data to a graphical program or virtual instrument using a graphical user interface, e.g., a front panel.

A graphical program may optionally have a GUI associated with the graphical program. In this case, the plurality of interconnected nodes are often referred to as the block diagram portion of the graphical program.

Data Flow Graphical Program (or Data Flow Diagram)—A graphical program or diagram comprising a plurality of interconnected nodes, where the connections between the nodes indicate that data produced by one node is used by another node.

Node—In the context of a graphical program, an element that may be included in a graphical program. The graphical program nodes in a graphical program may also be referred to as blocks. A node may have an associated icon that represents the node in the graphical program, as well as underlying code and/or data that implements functionality of the node. Exemplary nodes (or blocks) include function nodes, sub-program nodes (sub-VIs), terminal nodes, structure nodes, etc. Nodes may be connected together in a graphical program by connection icons or wires.

Graphical User Interface—this term is intended to have the full breadth of its ordinary meaning. The term "Graphical User Interface" is often abbreviated to "GUI". A GUI may include one or more input GUI elements, one or more output GUI elements, or both input and output GUI elements.

The following provides examples of various aspects of GUIs. The following examples and discussion are not intended to limit the ordinary meaning of GUI, but rather provide examples of what the term "graphical user interface" encompasses.

A GUI may comprise a single window having one or more GUI Elements, or may comprise more than one window each having one or more GUI Elements.

A GUI may be associated with a diagram, e.g., a graphical program. In this instance, various mechanisms may be used to connect GUI Elements in the GUI with nodes or icons in the diagram/graphical program. For example, when Input Controls and Output Indicators are created in the GUI, corresponding nodes (e.g., terminals) may be automatically created in the diagram or graphical program. Alternatively, the user can place terminal nodes in the diagram which may cause the display of corresponding GUI Elements front panel objects in the GUI, either at edit time or later at run time. As another example, the GUI may comprise GUI Elements embedded in the block diagram portion of the graphical program.

Front Panel—A Graphical User Interface that includes input controls and output indicators, and that enables a user to interactively control or manipulate the input being provided to a program or diagram, and view output of the program or diagram, during execution.

A front panel is a type of GUI. A front panel may be associated with a diagram or graphical program as described above.

In an instrumentation application, the front panel can be analogized to the front panel of an instrument. In an industrial automation application the front panel can be analogized to the MMI (Man Machine Interface) of a device. The user may adjust the controls on the front panel to affect the input, and view the output on the respective indicators.

Graphical User Interface Element—an element of a graphical user interface, such as for providing input or displaying output. Exemplary graphical user interface elements comprise input controls and output indicators Input Control—a graphical user interface element for providing user input to a program. Exemplary input controls comprise dials, knobs, sliders, switches, text input boxes, numeric input fields, etc.

Output Indicator—a graphical user interface element for displaying output from a program. Exemplary output indicators include charts, graphs, gauges, text output boxes, numeric displays, etc. An output indicator is sometimes referred to as an "output control".

Computer System—any of various types of computing or processing systems, including a personal computer (PC), mainframe computer system, workstation, laptop, network appliance, Internet appliance, personal digital assistant (PDA), television system, grid computing system, or other device or combinations of devices. In general, the term "computer system" can be broadly defined to encompass any device (or combination of devices) having at least one processor that executes instructions that are on memory medium.

Measurement Device—includes instruments, data acquisition devices, smart sensors, electrocardiogram monitoring equipment and any of various types of devices that are operable to acquire and/or store data. A measurement device may also optionally be further operable to analyze or process the acquired or stored data. Examples of a measurement device include an instrument, such as a traditional stand-alone "box" instrument, a computer-based instrument (instrument on a card) or external instrument, a data acquisition card, a device external to a computer that operates similarly to a data acquisition card, a smart sensor, one or more DAQ or measurement cards or modules in a chassis, an image acquisition device, such as an image acquisition (or machine vision) card, a video capture board, a smart camera, a motion control device, a robot having machine vision, and other similar types of devices. Exemplary "stand-alone" instruments include oscilloscopes, multimeters, signal analyzers, electrocardiogram monitors, arbitrary waveform generators, spectroscopes, and similar measurement, test, or automation instruments.

A measurement device may be further operable to perform control functions, e.g., in response to analysis of the acquired or stored data. For example, the measurement device may send a control signal to an external system, such as a motion control system or to a sensor, in response to particular data. A measurement device may also be operable to perform automation functions, i.e., may receive and analyze data, and issue automation control signals in response.

Embodiments of the present invention may be realized in any of various forms. For example, in some embodiments, the present invention may be realized as a computer-implemented method, a computer-readable memory medium, or a computer system. In other embodiments, the present invention may be realized using one or more custom-designed hardware devices such as ASICs or FPGA's.

A computer-readable memory medium is a memory medium that stores program instructions and/or data, where the program instructions, if executed by a computer system, cause the computer system to perform, e.g., any of a method embodiments described herein, or, any combination of the method embodiments described herein, or, any subset of any of the method embodiments described herein, or, any combination of such subsets.

In some embodiments, a computer system may be configured to include a processor (or a set of processors) and a memory medium. The memory medium stores program instructions. The processor is configured to read and execute the program instructions from the memory medium. The program instructions are executable to implement any of the various method embodiments described herein (or, any combination of the method embodiments described herein, or, any subset of any of the method embodiments described herein, or, any combination of such subsets). The computer system may be realized in any of various forms. For example, the computer system may be a personal computer (in any of its various realizations), a workstation, a computer on a card, an application-specific computer in a box, a server computer, a client computer, a hand-held device, a wearable computer, etc.

In some embodiments, a set of computers distributed across a network may be configured to partition the effort of executing a computational method (e.g., any of the method embodiments disclosed herein). In some embodiments, a first computer may be configured to acquire an ECG signal and send the resulting ECG signal data to a second computer over a network (such as the Internet). The second computer may operate on the ECG signal data according to any of the method embodiments described herein, or, any combination of the method embodiments described herein, or, any subset of any of the method embodiments described herein, or, any combination of such subsets.

Given two functions f and g (i.e., functions of time t), let <f,g> denote the inner product given by:

$$<f, g> = \int_{-\infty}^{\infty} f(t) g^*(t) dt, \quad (1)$$

where the superscript "*" denotes complex conjugation. The functions f and g are allowed to be complex functions. Thus, the inner product of two functions might be a complex number.

Let $\|f\|$ denote the function norm given by $\|f\|=(<f,f>)^{1/2}$. The function norm $\|*\|$ provides a means of measuring the "length" of a given function f. It also provides a means for measuring the distance between two functions f and g, i.e., $dist(f,g)=\|f-g\|$.

Given a real number $\tau$, a real number $\omega$ and a positive real number $\alpha$, let $h_{\tau,\omega,\alpha}$ be the function of time given by:

$$h_{\tau,\omega,\alpha}(t) = \sqrt[4]{\frac{\alpha}{\pi}} \exp\left[-\frac{\alpha}{2}(t-\tau)^2 + j\omega(t-\tau)\right]. \quad (2)$$

The notation exp[z] denotes the exponential function acting on the argument z. According to the above-specified norm, the function $h_{\tau,\omega,\alpha}$ has length one. The function $h_{\tau,\omega,\alpha}$ is a modulated Gaussian since it is the product of a Gaussian function $\exp[-(\alpha/2)(t-\tau)^2]$ and a complex sinusoid $\exp[j\omega(t-\tau)]$. The parameter $\tau$ is the center time of the Gaussian function. The parameter $\alpha$ represents the inverse variance of the Gaussian function, and thus, is a measure of the narrowness of the Gaussian function. The parameter $\omega$ is the frequency of the complex sinusoid.

Let K be the class of functions given by $$K=\{h_{\tau,\omega,\alpha}: \tau \text{ is real}, \omega \text{ is real}, \alpha \text{ is positive and real}\}. \quad (3)$$

Each vector $(\tau, \omega, \alpha)$ in the parameter space $G=R \times R \times R^+$ specifies a corresponding function $h_{\tau,\omega,\alpha}$ in class K. R denotes the set of real numbers. $R^+$ denotes the set of positive real numbers. The notation "A×B" denotes the Cartesian product of sets A and B.

Given an arbitrary function s(t) in the space of all continuous functions, one may imagine orthogonally projecting the function s(t) onto the linear subspace $L_{\tau,\omega,\alpha}$ (over the field of complex numbers) given by the function $h_{\tau,\omega,\alpha}$. Let $P_{\tau,\omega,\alpha}(s)$ denote the projection of function s onto the linear subspace $L_{\tau,\omega,\alpha}$. The projection $P_{\tau,\omega,\alpha}(s)$ is given by:

$$P_{\tau,\omega,\alpha}(s) = <s, h_{\tau,\omega,\alpha}> h_{\tau,\omega,\alpha}. \quad (4)$$

The length of the projection $P_{\tau,\omega,\alpha}(s)$ is given by $|<s, h_{\tau,\omega,\alpha}>|$, where $|z|$ denotes the absolute value of the complex number z.

Let $v_{opt}$ denote the vector $(\tau, \omega, \alpha)$ in the parameter space G that maximizes the projection length $|<s, h_{\tau,\omega,\alpha}>|$:

$$v_{opt} = \arg\max_{(\tau,\omega,\alpha) \in G} |<s, h_{\tau,\omega,\alpha}>|. \quad (5)$$

This patent specification discloses among other things a method for estimating the optimal parameter vector $v_{opt}$ in the situation where s(t) represents an electrocardiogram (ECG) signal or some portion of an ECG signal.

An ECG signal may have a waveform structure as suggested in FIG. 1. Observe that the waveform structure includes a number of waveform features such as a P wave, a QRS complex, a T wave and a U wave. The QRS complex is that portion of the structure that corresponds to the QRS interval. The definition of the QRS complex and the QRS interval are well understood from the literature of physiology and medicine.

The exact structure of an ECG signal will vary from person to person, and perhaps also from time to time in the same person. In some individuals, certain portions of the waveform structure may be missing or different in appearance or amplitude. For example, in some persons the U wave may be missing. In some persons, one or more portions of the QRS complex may be missing. Also, in certain states of cardiac disease, various portions of the waveform structure may be altered in form, altered in amplitude, or entirely missing.

Figure 2:
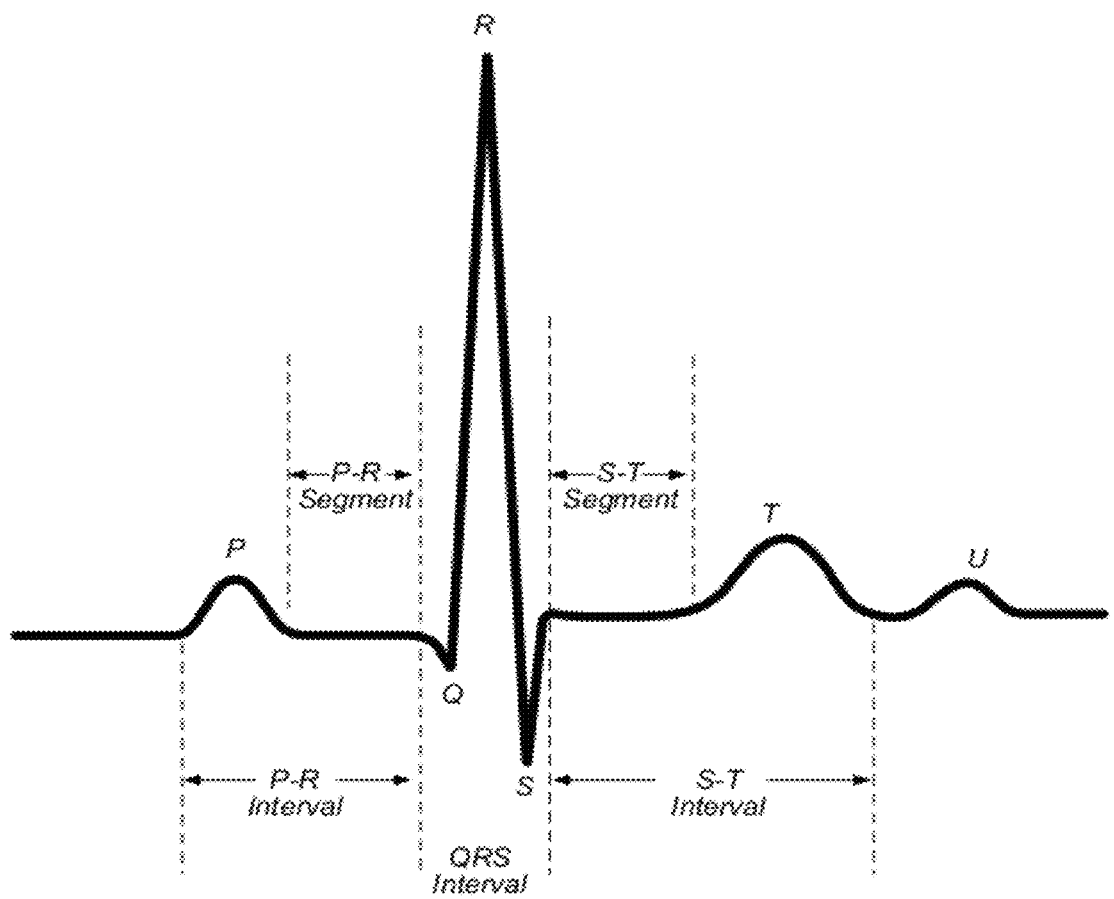
FIG. 2 shows an ECG signal with labels indicating the definitions of PR interval, PR segment, QRS interval, ST segment and ST interval.

FIG. 2 shows another example of an ECG signal, where the definitions of PR interval, PR segment, QRS interval, ST segment and ST interval are indicated.

Given a time-limited portion of an ECG signal s(t), e.g., the portion illustrated in FIG. 1, imagine approximating the signal s(t) by an expression of the form:

$$s(t) \approx 2\text{Re}\left[\sum_{j=1}^{N_P} <s, h_{v(j)}> h_{v(j)}(t)\right], \quad (6)$$

where the $N_P$ terms in the summation correspond to the $N_P$ most energetic features in the time-limited portion, e.g., features such as QRS complexes, T waves, P waves and U waves. (The notation Re[z] denotes the real part of the complex quantity z.) The vectors $v(1)$, $v(2)$, ..., $v(N_P)$ are optimal parameter vectors for the $N_P$ respective features. An appropriately-programmed computer system may compute the optimal parameter vectors $\{v(j)\}$ for the features (or some subset of the features) based on a method to be described below.

In some embodiments, the computer system may construct an approximating function x(t) for the signal s(t) based on the right hand side of expression (6). The approximating function x(t) may be displayed via a display device, e.g., in response to a user request.

In some embodiments, the optimal parameter vectors $\{v(j)\}$ and the corresponding coefficients $\{<s, h_{v(j)}>\}$ may be analyzed to determine which of the $N_P$ features correspond to QRS complexes (if any). Each parameter vector v that is identified as corresponding to a QRS complex may be used to estimate the onset and offset time of that QRS complex. For example, given that vector $v=(\tau, \omega, \alpha)$ is identified as corresponding to a QRS complex, the onset and offset times for the QRS complex may be estimated based on the expressions:

$$t_{onset} = \tau - k_{QRS}\sqrt{\frac{1}{\alpha}} \quad (7A)$$

$$t_{offset} = \tau + k_{QRS}\sqrt{\frac{1}{\alpha}}, \quad (7B)$$

where $k_{QRS}$ is a positive constant.

In some embodiments, the computer system may compute an onset time and offset time for each of the $N_P$ features. The onset time and offset time for any given one of the features may be computed based on the optimal delay time $\tau$ and the optimal $\alpha$ of that feature using equations (7A) and (7B).

The number $N_P$ is greater than or equal to one. The number $N_P$ may depend on the duration of the time-limited portion, i.e., the captured portion, of the ECG signal. If an estimate of heart rate is available, the number $N_P$ may depend on the estimated heart rate. The number $N_P$ may also depend on the species of organism under analysis and/or on an operational mode selection.

In some embodiments, $N_P$ is an integer in the range [1,50].

In one embodiment, where the ECG signal corresponds to the human heart, $N_P$ is set equal to an integer in the range from floor ((3 sec$^{-1}$)*$T_B$) to ceiling ((6 sec$^{-1}$)*$T_B$) inclusive, where $T_B$ is the time duration of the time-limited portion. For example, if the time-limited portion is one-second in duration, then $N_P$ may be a value in the range [3,6]. A wide variety of other ranges are contemplated as well.

In some embodiments, a method for analyzing an ECG signal may include a coarse estimation process and a refinement process. The coarse estimation process may operate as outlined by the pseudo-code in FIG. 3.

At line 310, a computer system may receive a block $\{s(n)\}$ of samples of an ECG signal s. (The index n is the discrete time index.) Let $N_S$ denote the number of samples in the received block.

At lines 320-355, the computer system may perform a multiscale short-time Fourier transform (STFT) on the sample block $\{s(n)\}$ to obtain a transform array S:

$$S=\{S[i,j,k]: i=0, \ldots, N_{WS}-1; j=0, \ldots, N_\tau-1; k=0, \ldots, N_\omega-1\}. \quad (8)$$

The values S[i,j,k] of the array S are complex numbers. The first index i corresponds to window size. $N_{WS}$ denotes the number of different window sizes that are used in the multiscale STFT.

Window size may be measured from the center of the window to the right (or left) shoulder of the window (or, alternatively, from the left shoulder to the right shoulder).

The second index j corresponds to delay time $\tau$ (also referred to herein as "window displacement time"). $N_\tau$ denotes the number of delay times that are used in the multiscale STFT. The third index k corresponds to frequency $\omega$. $N_\omega$ denotes the number of distinct frequencies used in the multiscale STFT.

The multiscale STFT uses a window function w(n). The window function may be nominally centered at time zero. In one embodiment, the window function is a Gaussian window. In other embodiments, the window function may be a raised cosine window, a polynomial window, a rational function window, a Hamming window, a Hann window, a Lanczos window, a Blackman window, etc.

The multiscale STFT uses an array of window sizes, $\{\sigma(i): i=0, \ldots, N_{WS}-1\}$. The number $N_{WS}$ is typically greater than two. In some embodiments, $N_{WS}$ equals three. In other embodiments, $N_{WS}$ equals an integer in the interval [4,8]. In another embodiment, $N_{WS}$ is an integer less than or equal to 256. In one embodiment, the array of window sizes is given by $\{0.05$ sec, $0.1$ sec, $0.2$ sec$\}$.

The multiscale STFT also uses an array of $\tau$ values, $\{\tau(j): j=0, \ldots, N_\tau-1\}$. For example, in some embodiments, the array of $\tau$ values is given by $\{j*STEP_\tau: j=0, \ldots, N_\tau-1\}$, where $STEP_\tau$ is the step size for delay time $\tau$. In one embodiment, the value $STEP_\tau$ may be a value which is equal to 0.125*window size. In some embodiments, the value $STEP_\tau$ is in the range from 6 milliseconds to 25 milliseconds. However, values outside that range are contemplated as well.

As shown at 330-340, for each pair (i,j) in $\{0, \ldots, N_{WS}-1\} \times \{0, \ldots, N_\tau-1\}$, the computer system may operate on the block $\{s(n)\}$ to generate a localized signal $\{y(n)\}$ according to the expression:

$$y(n) = s(n)w\left(\frac{n-\tau(j)}{\sigma(i)}\right), \quad (9)$$

$$n = 0, 1, \ldots, N_s - 1.$$

In other words, the signal samples $\{s(n)\}$ are multiplied by a horizontally scaled and time-shifted version of the window function w. The amount of the time shift is determined by $\tau(j)$ and the amount of horizontal scaling is controlled by $\sigma(i)$.

At 345, the computer system may perform a discrete-time Fourier transform (e.g., an FFT) on the localized signal y. The vector result of the Fourier transform is stored in the vector S[i,j,*].

At 365, the computer system may search the magnitude array |S[i,j,k]| over the (i,j,k) space to determine $N_P$ distinct peaks (or local maxima), e.g., the $N_P$ largest peaks. Each peak P (or local maximum) is characterized by a frequency value $\omega_P$, a delay time value $\tau_P$, a window width value $\sigma_P$, and an amplitude (or power) value $A_P$. The frequency value $\omega_P$ specifies the location of the peak P in the frequency dimension. The window width value $\sigma_P$ specifies the location of the peak P in the window-width dimension. The delay time $\tau_P$ specifies the location of the peak in the delay-time dimension.

The window width may be measured from the center of the window to a shoulder of the window (or alternatively, from the left shoulder to the right shoulder of the window). For example, for a Gaussian window function, the standard deviation may be taken as the window width.

In some embodiments, the computer system may search the square magnitude array $|S[i,j,k]|^2$ instead of the magnitude array |S [i,j,k]|. The square magnitude array may be convenient to use since it can be computed without a square root operation. (Recall that $|z|^2 = zz^*$.)

In some embodiments, the computer system may constrain the search to a predetermined frequency interval to increase the likelihood of locating a peak (or local maximum) that corresponds to a QRS complex. For example, in one embodiment, the computer system searches over the frequency interval [10 Hz, 25 Hz].

In some embodiments, the computer system may impose one or more time constraints on the search for peaks. For example, the computer system may require that the separation of the peaks in delay time be at least $\Delta T_{min}$, where $\Delta T_{min}$ is the minimum attainable separation time between any two adjacent waveform features in the ECG signal.

As noted above, the method for analyzing an ECG signal may include a refinement process in addition to the coarse estimation process just described. In one set of embodiments, the refinement process operates on the frequency value $\omega_P$, the delay time value $\tau_P$ and the window width value $\sigma_P$ of each peak P to determine a refined estimate for the delay time and a refined estimate for the window width value. The refinement process may be implemented as follows.

First, the computer system may compute inner products of the sample block {s(n)}, respectively, with three particular functions from the class K:

$$z_0 = <s, h_{\tau_P, \omega_P, \alpha_P}>, \quad (10A)$$

$$z_{+1} = <s, h_{\tau_P + \Delta\tau, \omega_P, \alpha_P}>, \quad (10B)$$

$$z_{-1} = <s, h_{\tau_P - \Delta\tau, \omega_P, \alpha_P}>, \quad (10C)$$

where $\alpha_P$ is equal to or proportional to $(1/\sigma_P)^2$, where $\Delta\tau$ is a positive value. For example, in one embodiment, $\Delta\tau$ is a value in the interval $(0, \sigma_P]$. In another embodiment, $\Delta\tau$ is a value in the interval $(0, 2\sigma_P]$.

Second, the computer system may solve the following linear system:

$$\begin{bmatrix} \Delta\tau & (\tau_P - \Delta\tau)^2 - \tau_P^2 \\ -\Delta\tau & (\tau_P - \Delta\tau)^2 - \tau_P^2 \end{bmatrix} \begin{bmatrix} x_f \\ b \end{bmatrix} = \begin{bmatrix} \ln\frac{|z_0|}{|z_{-1}|} \\ \ln\frac{|z_0|}{|z_{+1}|} \end{bmatrix}. \quad (11)$$

Third, the computer system may compute the refined estimate $\tau_f$ for delay time and the refined estimate $d_f$ for window width based on the expressions:

$$\tau_f = 2b/x_f \quad (12A)$$

$$d_f = [(\alpha_P - 2b)/2b\alpha_P]^{1/2} \quad (12B)$$

The computer system may also compute a refined amplitude $A_f$ for the peak P based on the expression:

$$A_f = <s, h_{\tau_f, \omega_P, \alpha_f}>, \quad (13)$$

where $\alpha_f = (1/d_f)^2 = 2b\alpha_P/(\alpha_P - 2b)$.

After computing the refined delay and the refined window width for each peak P, the computer system may identify which of the peaks correspond to a QRS complex.

In some embodiments, the computer system may identify a peak as corresponding to a QRS complex if its amplitude $A_P$ (or refined amplitude $A_f$) is larger than a threshold value. In one embodiment, the threshold value may be a fixed value determined by experimentation. In another embodiment, the threshold value may be determined by user input. In yet another embodiment, the threshold value may be a predetermined fraction of $A_{MAX}$, where $A_{MAX}$ is the maximum of the amplitudes $\{A_P\}$ (or refined amplitudes) of the $N_P$ peaks. In yet another embodiment, the threshold value may be a predetermined fraction of the amplitude (or refined amplitude) of the previously-identified QRS complex. In yet another embodiment, the threshold value may be a predetermined fraction of an FIR or IIR filtration of the amplitudes (or refined amplitudes) of previously-identified QRS complexes.

In some embodiments, the computer system may also require that the refined delay time $\tau_f$ of a peak satisfy one or more time constraints in order to be identified as a QRS complex. For example, if a previously identified QRS complex occurred at time t=10 seconds, it would be impossible for a peak occurring at time t=10.01 seconds to be a QRS complex because the minimum QRS repetition interval is significantly larger than 0.01 seconds.

Figure 4:
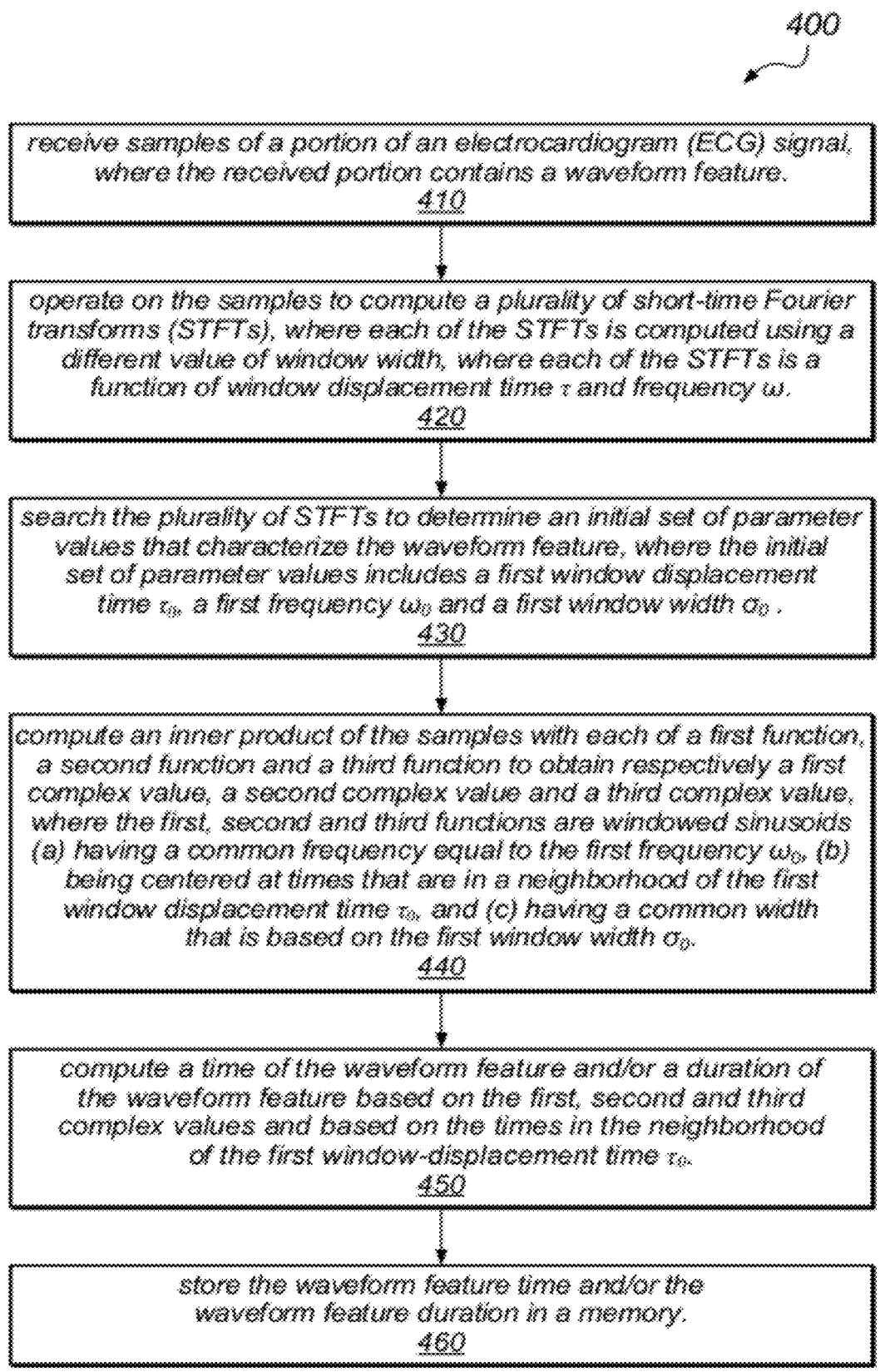
FIG. 4 illustrates one embodiment of a method for detecting a QRS complex in an ECG signal.

In one set of embodiments, a method 400 for estimating the time of a waveform feature in an ECG signal may include the following operations. See FIG. 4.

At 410, a computer system may receive a set of samples of a portion of an electrocardiogram (ECG) signal. The received portion of the ECG signal contains a waveform feature. The number $N_S$ of samples in the sample set may be an integer based on sampling rate. For example, in one embodiment, $N_S$ equals 250 if the sampling rate is 250 samples per second. In some embodiments, the number $N_S$ is selected to guarantee that at least one QRS complex is contained with the sample set.

At 420, the computer system operates on the samples to compute a plurality of short-time Fourier transforms (STFTs). Each of the STFTs is computed using a different value of window width. Each of the STFTs is a function of window displacement time $\tau$ and frequency $\omega$. The STFTs may be computed using Fast Fourier Transforms (FFTs).

In one embodiment, three STFTs are computed, using window widths of 0.2 sec, 0.1 sec and 0.05 sec respectively. However, other numbers of STFTs may be computed, and other sets of window width values may be used.

In some embodiments, the signal samples are subjected to filtering for baseline removal prior to the computation of the STFTs.

At 430, the computer system may search the plurality of STFTs to determine an initial set of parameter values that characterize the waveform feature, where the initial set of parameter values includes a first window displacement time $\tau_0$, a first frequency $\omega_0$ and a first window width $\sigma_0$. In one embodiment, the search process 430 may involve: computing the magnitude of the STFTs to obtain respective magnitude spectra; and searching for a peak (e.g., local or global maximum) in the magnitude spectra. The location of the peak in the ($\tau$, $\omega$, window width) space may determine the initial set of parameters.

The search process 430 may also involve smoothing the magnitude spectra before searching for the peak. The smoothing operation may allow the peak to be more reliably located.

In some embodiments, the search process 430 is restricted to frequencies in a predetermined range of frequencies. For example, when the ECG signal is a human ECG signal, the search process may be restricted to frequencies in the range [10 Hz, 25 Hz]. In another embodiment, the search process is restricted to the range [8 Hz, 30 Hz]. Different ranges may be used in different application contexts.

At 440, the computer system may compute an inner product of the samples with each of a first function, a second function and a third function to obtain respectively a first complex value, a second complex value and a third complex value. The first, second and third functions are windowed sinusoids (a) having a common frequency equal to the first frequency $\omega_0$, (b) being centered at times that are in a neighborhood $U(\tau_0)$ of the first window displacement time $\tau_0$, and (c) having a common width that is based on the first window width $\sigma_0$.

In one embodiment, the first, second and third complex values may be computed according to the following expressions:

$$<s(n), f_1(n)>, \qquad (14A)$$

$$<s(n), f_2(n)>, \qquad (14B)$$

$$<s(n), f_3(n)>, \qquad (14C)$$

where s represents the ECG signal, where $f_1$, $f_2$ and $f_3$ represent the first, second and third functions respectively. The notation $<x(n), y(n)>$ represents the inner product given by $$\sum_{n=1}^{N_s} x(n) y(n). \qquad (15)$$

At 450, the computer system may compute a time of the waveform feature and/or a duration of the waveform feature based on the first, second and third complex values and based on the times in the neighborhood $U(\tau_0)$ of the first window-displacement time $\tau_0$. In some embodiments, the computer system may compute the waveform feature time and the waveform feature duration by solving a linear system $Av=c$ for the unknown vector v, where the matrix A is determined by the times in the neighborhood $U(\tau_0)$ of the first window-displacement time $\tau_0$, where the vector c is determined by the first, second and third complex values.

The neighborhood $U(\tau_0)$ may be an interval of the form $[\tau_0 - \epsilon, \tau_0 + \epsilon]$, where $\epsilon$ is proportional to $\sigma_0$. In one embodiment, the times in the neighborhood $U(\tau_0)$ include the times $\tau_0$, $\tau_1$ and $\tau_{-1}$, where $\tau_1 = \tau_0 + \Delta\tau$ and $\tau_{-1} = \tau_0 - \Delta\tau$, where $\Delta\tau = r\sigma_0$. In this embodiment, the matrix A and the vector c may be determined by the expressions:

$$A = \begin{bmatrix} \tau_0 - \tau_{-1} & \tau_{-1}^2 - \tau_0^2 \\ \tau_0 - \tau_1 & \tau_1^2 - \tau_0^2 \end{bmatrix}, \qquad (16A)$$

$$c = [\ln|z_0|/|z_{-1}|, \ln|z_0|/|z_{+1}|]^T, \qquad (16B)$$

where $\ln(*)$ denotes the natural logarithm function, where complex value $z_0$ is the inner product corresponding to time $\tau_0$, where complex value $z_1$ is the inner product corresponding to time $\tau_1$, where complex value $z_{-1}$ is the inner product corresponding to time $\tau_{-1}$. Thus, the solution vector v is given by $v = A^{-1}c$, where $A^{-1}$, the inverse of matrix A, is given by:

$$A^{-1} = \frac{\begin{bmatrix} \tau_1^2 - \tau_0^2 & -\tau_{-1}^2 + \tau_0^2 \\ -\tau_0 + \tau_1 & \tau_0 - \tau_{-1} \end{bmatrix}}{(\tau_0 - \tau_{-1})(\tau_1^2 - \tau_0^2) - (\tau_0 - \tau_1)(\tau_{-1}^2 - \tau_0^2)}. \qquad (17)$$

As noted above, $\Delta\tau = r\sigma_0$. In one embodiment, the parameter r equals 0.1. However, a wide variety of other values are contemplated for the parameter r. For example, in one set of embodiments, r may take a value in the range [0.08, 0.12]. In another set of embodiments, r may take a value in the range [0.05, 0.2]. In yet another set of embodiments, r may take a value in the range [0.033, 0.3].

Let $x_\tau$ and b denote the first and second components of v, respectively, i.e., $v = [x_f, b]^T$. The computer system may compute the waveform feature time $\tau_f$ and the waveform feature duration $d_f$ based on the expressions:

$$\tau_f = 2b/x_f \qquad (18A)$$

$$d_f = [(\alpha_0 - 2b)/2b\alpha_0]^{1/2} \qquad (18B)$$

In some embodiments, the computer system may utilize more than three times in the neighborhood $U(\tau_0)$. Thus, instead of a 2×2 system, the computer system may generate and solve an m×2 system, where m is greater than two. Since an m×2 system is overdetermined (more equations than unknowns), the computer system may compute the least squares solution v* to the system $Av=c$. Methods for computing the least squares solution for an overdetermined linear system are well known in the art.

At 460, the computer system may store the waveform feature time and the waveform feature duration in a memory. The waveform feature time and/or the waveform feature duration may be subsequently accessed from the memory for further processing. For example, the waveform feature time may be used together with one or more previous waveform feature times to estimate a heart rate.

In some embodiments, the computer system displays the waveform feature time (or a value derived from the waveform feature time) via a display device. For example, the waveform feature time may be displayed as a numeric value. As another example, the waveform feature time may be indicated by placing a marker (e.g., an arrow or a point) on the time axis of a displayed graph of the ECG signal. The position of the marker on the time axis indicates the waveform feature time.

In some embodiments, the computer system also displays the waveform feature duration via the display device. For example, the waveform feature duration may be displayed as a numeric value. As another example, the waveform feature duration may be indicated by highlighting (or otherwise marking) an interval on the time axis of a displayed graph of the ECG signal. As yet another example, the waveform feature duration may be indicated by highlighting a portion of the waveform itself on a displayed graph of the ECG signal.

The waveform feature may any of a variety of features that occur within ECG signals. For example, the waveform feature may be a QRS complex, a T wave, a P wave or a U wave. In the case where the waveform feature is a QRS complex, the computer system may compute an onset time and/or an offset time of the QRS complex based on the waveform feature time and the waveform feature duration. For example, the onset time and the offset time may be computed according the relations:

$$t_{onset} = \tau_f - kd_f \quad (19A)$$

$$t_{offset} = \tau_f + kd_f. \quad (19B)$$

The value k may be a value in the range [2.5, 5.0]. For example, in one embodiment, k equals 4. In another embodiment k equals 3.5. In some embodiments, the value k may depend on a current estimate of heart rate and/or on the species of the organism under analysis. In some embodiments, the value k may depend on a type of cardiac pathology. (For example, a user may select the type of cardiac pathology from a list of known types.)

In some embodiments, the plurality of STFTs are computed using Gaussian windows. However, other window types are contemplated. For example, in other embodiments, the STFTs may use raised cosine windows, polynomial windows, rational function windows, trapezoidal windows, triangular windows, etc.

In some embodiments, the windowed sinusoid functions that are used to calculate the inner products are Gaussian-modulated complex exponentials, e.g., members of the class K as described above. Other types of modulation are contemplated. For example, in other embodiments, the windowed sinusoid functions are complex exponentials that are modulated with raised cosine windows, polynomial windows, rational function windows, trapezoidal windows, triangular windows, etc.

Figure 5:
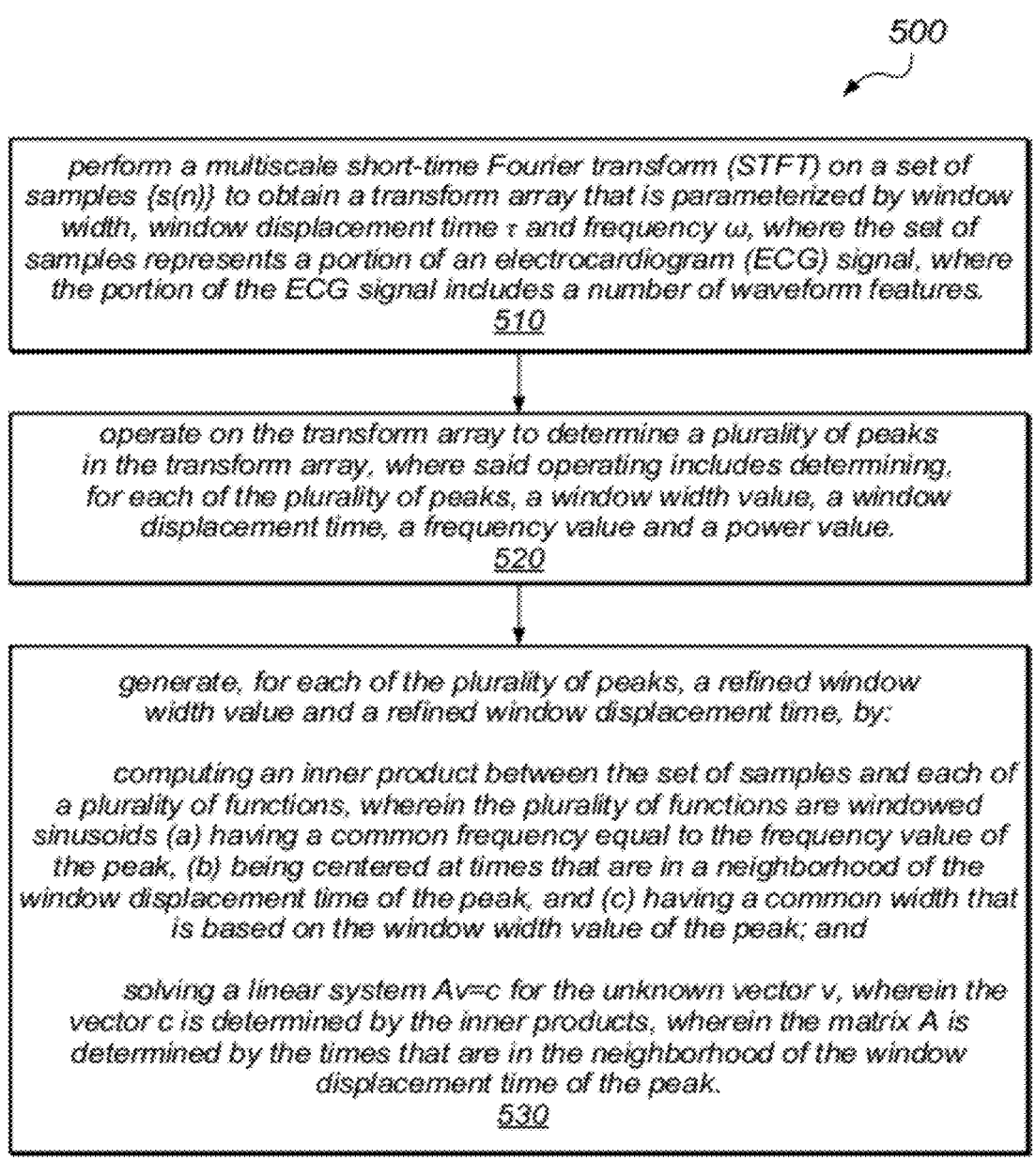
FIG. 5 illustrates one embodiment of a method for generating characterizing parameters for a set of waveform features in an ECG signal.

In one set of embodiments, a method 500 for identifying a QRS complex may include the following operations. See FIG. 5.

At 510, a computer system may perform a multiscale short-time Fourier transform (STFT) on a set of samples $\{s(n)\}$ to obtain a transform array that is parameterized by window width, window displacement time $\tau$ and frequency $\omega$. In one embodiment, the multiscale STFT includes three monoscale STFTs based on window widths of 0.2 sec, 0.1 sec and 0.05 sec, respectively. However, the multiscale STFT may include other numbers of monoscale STFTs; and other sets of window width values may be used.

In some embodiments, the sample set $\{s(n)\}$ is subjected to filtering for baseline removal prior to performing the multiscale STFT.

The sample set $\{s(n)\}$ may represent a portion of an ECG signal. The ECG signal portion may include a number of waveform features. For example, the waveform features may include at least one QRS complex. The waveform features may also include other features such as one or more instances of the following types of features: T waves, P waves and U waves.

As noted above, the multiscale STFT may be computed by performing a number of FFTs.

At 520, the computer system may operate on the transform array to determine a plurality of peaks in the transform array. The process of operating on the transform array may include determining, for each of the plurality of peaks, a window width value, a window displacement time, a frequency value, and a power value (or amplitude value).

In some embodiments, the process 520 of operating on the transform array may include searching for the $N_P$ peaks (or local maxima) of largest magnitude in the transform array. In other words, the computer system may compute a magnitude array from the transform array (by calculating the magnitude of each complex entry of the transform array), and then identify the $N_P$ largest peaks in the magnitude array. As noted above, smoothing may be applied to the magnitude array prior to identifying the peaks.

In some embodiments, the search for peaks in the transform array may be restricted to a band of frequencies that is smaller than the frequency range of the multiscale STFT. For example, when the ECG signal is a human ECG signal, the search process may be restricted to frequencies in the band [10 Hz, 25 Hz]. In another embodiment, the search process is restricted to the band [8 Hz, 30 Hz]. Different bands may be used in different application contexts.

At 530, the computer system may generate, for each of the plurality of peaks, a refined window width value and a refined window displacement time, by: computing an inner product between the set of samples and each of a plurality of functions. The plurality of functions may be windowed sinusoids (a) having a common frequency equal to the frequency value of the peak, (b) being centered at times that are in a neighborhood of the window displacement time of the peak, and (c) having a common width that is based on the window width value of the peak; and solving a linear system Av=c for the unknown vector v, where the vector c is determined by the inner products, where the matrix A is determined by the times that are in the neighborhood of the window displacement time of the peak.

In some embodiments, the windowed sinusoids are Gaussian-modulated complex exponentials. In other embodiments, the windowed sinusoid functions are complex exponentials that are modulated with raised cosine windows, polynomial windows, rational function windows, trapezoidal windows, triangular windows, etc.

In some embodiments, the computer system may identify one of the peaks (or local maxima) as corresponding to a QRS complex based on a determination that the power value of the peak exceeds a threshold value. The computer system may also require that the refined window displacement time of the peak satisfies one or more time constraints in order to qualify as a QRS complex.

In one embodiment, the threshold value for power is an adaptive threshold that changes over time. For example, the threshold value may be dynamically adjusted based on the power values computed for previous QRS complexes in the ECG signal.

The one or more time constraints may include a constraint on the QRS repetition interval. Thus, in order for a peak to qualify as a QRS complex, the computer system may require that the refined window displacement time of the peak occurs within a time interval $[t_{prev}+T_A, t_{prev}+\text{The value } T_B]$. The value $t_{prev}$ represents a time that has been determined for a previous QRS complex. The value $T_A$ is the minimum time between two successive QRS complexes. The value $T_B$ is the maximum time between two successive QRS complexes. The values $T_A$ and $T_B$ may be determined based on a maximum heart rate $R_{max}$ and a minimum heart rate $R_{min}$ according to the relations:

$$T_A = 1/R_{max} \quad (20A)$$

$$T_B = 1/R_{min}. \quad (20B)$$

In some embodiments, the maximum rate $R_{max}$ and the minimum rate $R_{min}$ may be set by a user/operator. In one embodiment, the maximum rate and minimum rate are determined by a mode selection. The user may be offered a choice from a number of supported modes. For example, in one mode, appropriate for a "normal" human heart, the minimum rate may be 50 Hz and the maximum rate may be 200 Hz.

In some embodiments, the values $T_A$ and $T_B$ may be adaptive constants. Their values may change based on the actual repetition intervals observed from the QRS complexes that have been previously identified by the computer system.

In some embodiments, the one or more time constraints for QRS identification may include a constraint on the PR interval, i.e., the time from the P wave to the following QRS complex. Thus, in the case where a waveform feature X of sub-threshold power (e.g., a P wave) has been identified, the computer system may require that the refined window displacement time corresponding to a peak be at least $T_{PR}$ seconds after the time of the waveform feature X, where $T_{PR}$ is a minimum value for the PR interval. In one embodiment, the computer system may also impose a maximize value constraint on the PR interval.

In some embodiments, the one or more time constraints for QRS identification may include a constraint on the QT interval, i.e., the time from the QRS complex to the following T wave. Thus, in the case where a waveform feature Y of sub-threshold power (e.g., a T wave) has been identified, the computer system may require that the refined window displacement time corresponding to a peak be at least $T_{QT}$ seconds before the time of the waveform feature Y, where $T_{QT}$ is a minimum value for the QT interval. In one embodiment, the computer system may also impose a maximize value constraint on the QT interval.

In some embodiments, the computer system may compute a QRS onset time and/or a QRS offset time based on the refined window displacement time and the refined window width of the QRS peak (i.e., the peak that has been identified as corresponding to the QRS complex). The computer system may display the QRS onset and/or the QRS offset time via a display device. In one embodiment, the QRS onset and QRS offset time may be indicated by adding time markers to a displayed graph of the ECG signal. For example, the markers may be arrows or vertical lines that indicate the QRS onset and offset times on the displayed graph.

In some embodiments, the computer system may repeat processes 510, 520 and 530 for a series of sets of samples of the ECG signal, i.e., for a series of sample blocks. In one embodiment, successive sample sets are partially overlapping.

As described above, process 520 determines a plurality of peaks. Let $\{P_j\}$ denote the plurality of peaks. In some embodiments, the computer system may compute a windowed sinusoid function $h_j$ for each peak $P_j$, where the windowed sinusoid function is determined by the refined window width value of the peak, the refined window displacement time of the peak, and the frequency value of the peak. (For example, the functions $\{h_j\}$ may be functions of the class K as described above.) Furthermore, the computer system may generate a linear combination of the windowed sinusoid functions $\{h_j\}$ according to the expression $$\sum_{j=1}^{N_P} c_j h_j(n), \quad (21)$$

where the coefficients $\{c_j\}$ of the linear combination are determined by the power values of the corresponding peaks $\{P_j\}$. For example, $c_j$ may be set equal to $SQRT(P_j)$. Alternatively, the coefficient $c_j$ may be set equal to the inner product $<s,h_j>$. The computer system may display a graph of real part of the linear combination as a function of time.

Figure 6:
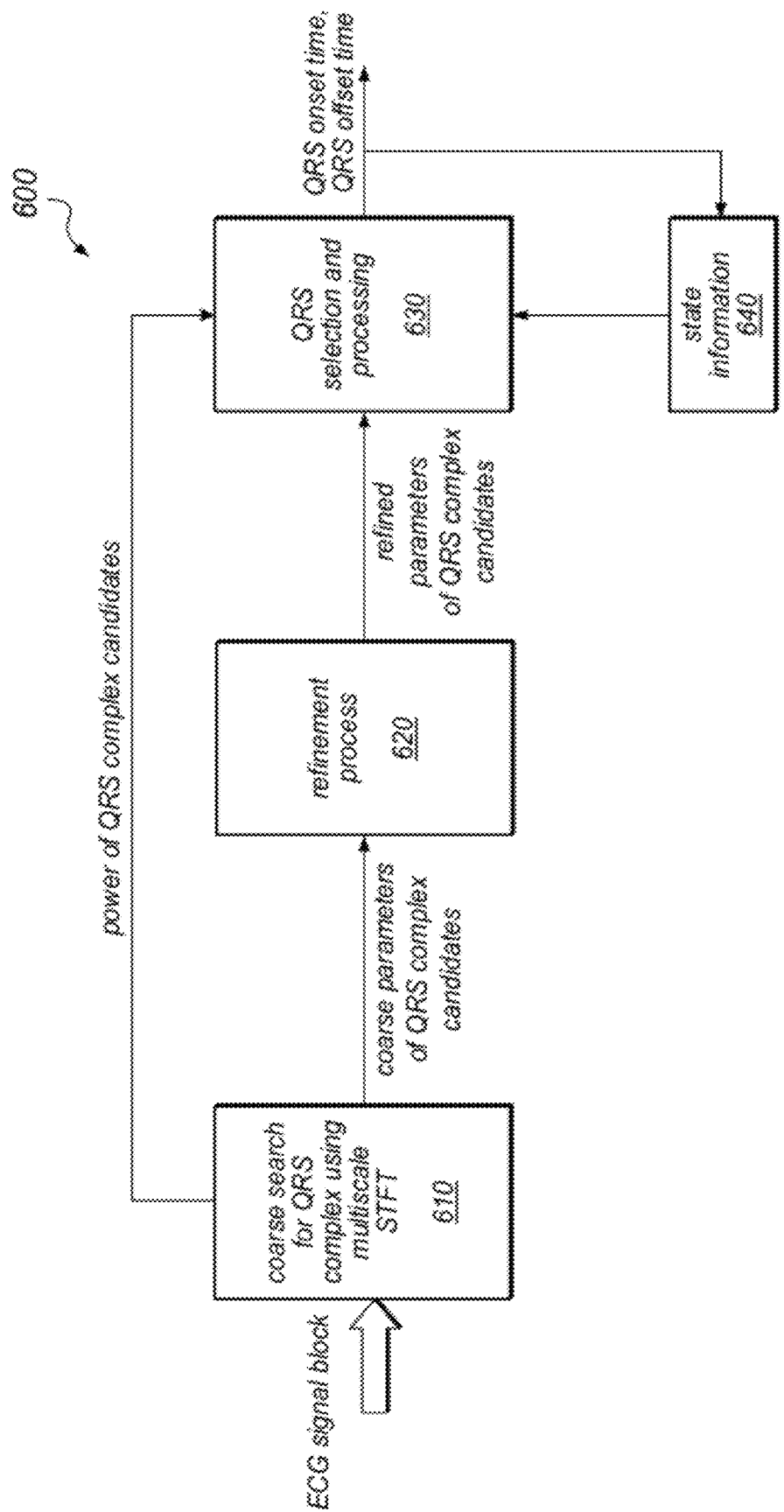
FIG. 6 illustrates one exemplary block diagram for a system of processing ECG signals to determine QRS onset and offset times.

FIG. 6 is a block diagram illustrating a method 600 for analyzing an ECG signal to determine QRS onset and offset times. The method 600 may be performed by a computer system or an interacting set of computer systems.

Process 610 receives a block of samples of an ECG signal and performs a coarse search for the QRS complex using a multiscale STFT. The coarse search may be performed as variously described above. The coarse search identifies a set of QRS complex candidates, and generates coarse parameters for each candidate, e.g., parameters such as window width, window displacement time (also known as delay time) and frequency.

Process 620 operates on the coarse parameters of each QRS complex candidate to generate corresponding refined parameters for the candidate. Thus, process 620 may be referred to herein as a "refinement process". The refined parameters for a candidate may include a refined window width and a refined window displacement time. The frequency $\omega_P$ of a candidate may also be interpreted as a refined parameter although its value is not changed by the refinement process. The refinement process may be implemented as variously described above.

Processor 630 selects the one of the candidates as the QRS complex based on an analysis of the refined parameters and the power values (or amplitude values) of the candidates. Process 630 may also calculate a QRS onset time and a QRS offset time based on the refined parameters of the QRS winner (i.e., the selected candidate). Process 630 may be implemented as variously described above.

In some embodiments, the QRS onset time and QRS offset time from one or more previously identified QRS complexes may be stored as state information. Furthermore, the coarse power values (or the refined amplitude values) of one or more previously identified QRS complexes may be stored as part of the state information. The state information may be used by process 630 in performing the current QRS selection.

Figure 7:
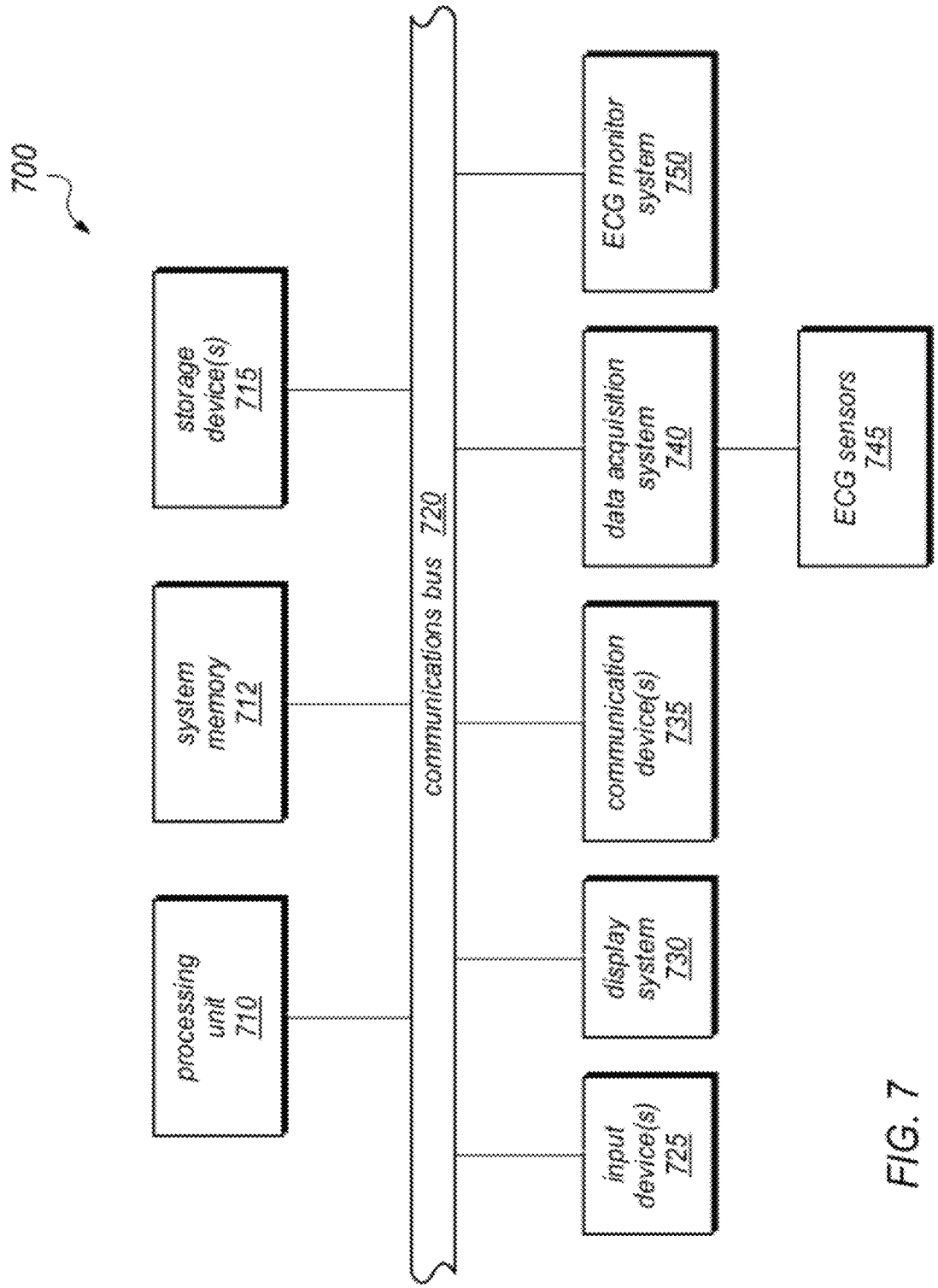
FIG. 7 illustrates one embodiment of a computer system for performing any of the method embodiments described herein.

FIG. 7 illustrates one embodiment of a computer system 700 that may be used to perform any of the method embodiments described herein, or, any combination of the method embodiments described herein, or any subset of any of the method embodiments described herein, or, any combination of such subsets.

Computer system 700 may include a processing unit 710, a system memory 712, a set 715 of one or more storage devices, a communication bus 720, a set 725 of input devices, and a display system 730.

System memory 712 may include a set of semiconductor devices such as RAM devices (and perhaps also a set of ROM devices).

Storage devices 715 may include any of various storage devices such as one or more memory media and/or memory access devices. For example, storage devices 715 may include devices such as a CD/DVD-ROM drive, a hard disk, a magnetic disk drive, magnetic tape drives, etc.

Processing unit 710 is configured to read and execute program instructions, e.g., program instructions stored in system memory 712 and/or on one or more of the storage devices 715. Processing unit 710 may couple to system memory 712 through communication bus 720 (or through a system of interconnected busses). The program instructions configure the computer system 700 to implement a method, e.g., any of the method embodiments described herein, or, any combination of the method embodiments described herein, or, any subset of any of the method embodiments described herein, or any combination of such subsets.

Processing unit 710 may include one or more processors (e.g., microprocessors).

One or more users may supply input to the computer system 700 through the input devices 725. Input devices 225 may include devices such as a keyboard, a mouse, a touch-sensitive pad, a touch-sensitive screen, a drawing pad, a track ball, a light pen, a data glove, eye orientation and/or head orientation sensors, a microphone (or set of microphones), or any combination thereof.

The display system 730 may include any of a wide variety of display devices representing any of a wide variety of display technologies. For example, the display system may be a computer monitor, a head-mounted display, a projector system, a volumetric display, or a combination thereof. In some embodiments, the display system may include a plurality of display devices. In one embodiment, the display system may include a printer and/or a plotter.

In some embodiments, the computer system 700 may include other devices, e.g., devices such as one or more graphics accelerators, one or more speakers, a sound card, a video camera and a video card.

The various display actions described herein may be performed using the display system 730.

In some embodiments, computer system 700 may include one or more communication devices 735, e.g., a network interface card for interfacing with a computer network. In one embodiment, computer system 700 may receive ECG signal samples from a remote computer via such a communication device.

The computer system may be configured with a software infrastructure including an operating system, and perhaps also, one or more graphics APIs (such as OpenGL®, Direct3D, Java 3D™)

In some embodiments, the computer system 700 may be configured for coupling to a data acquisition system 740. The data acquisition system 740 is configured to receive analog inputs signals, to digitize the analog input signals, and to make those digitized signals available to the computer system 700. For example, the data acquisition system 740 may interface with a set of ECG sensors 745 in order to capture ECG signals that are provided by the ECG sensors 745. The data acquisition system 740 may operate under the control of the software executing on processor 710.

In some embodiments, the computer system 700 may be configured to interface with a specialized ECG monitor system 750, e.g., an off-the-shelf system designed for capturing and/or monitoring ECG signals.

Figure 8:
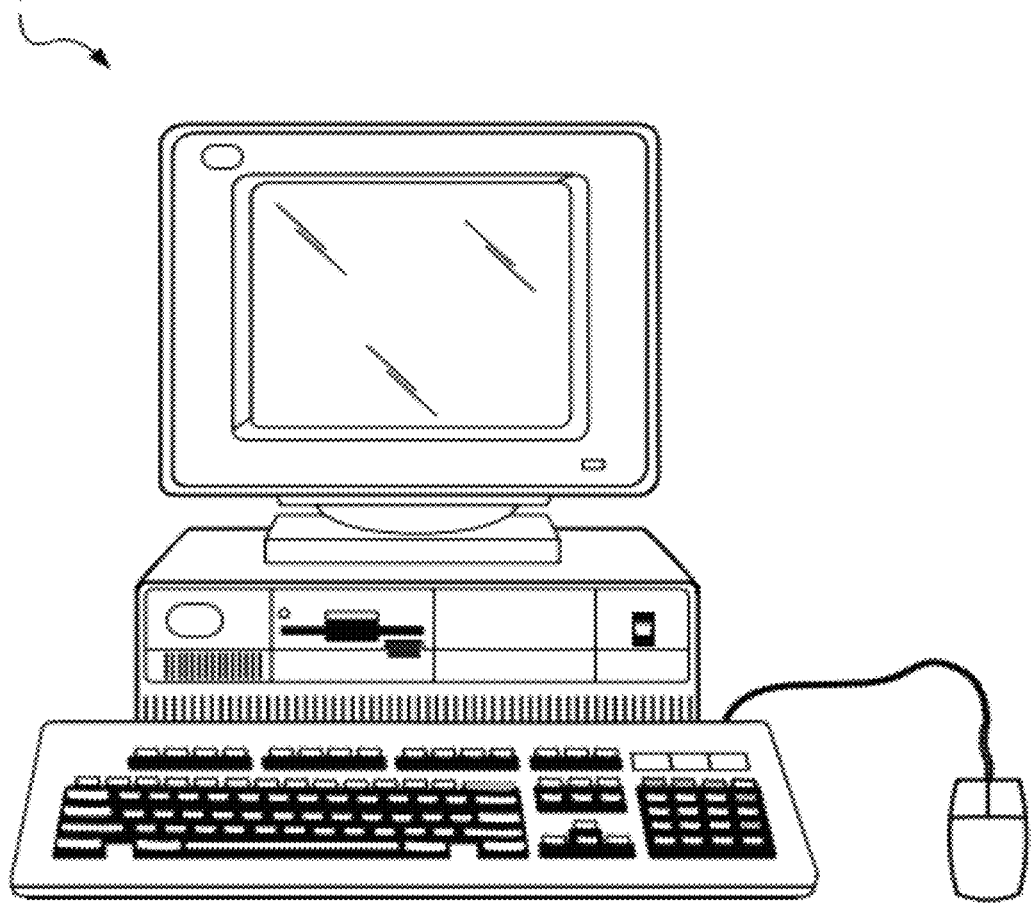
FIG. 8 illustrates one embodiment of a computer system 700A for performing any of the method embodiments described herein.

FIG. 8 illustrates one possible embodiment 700A for computer system 700.

Figure 9:
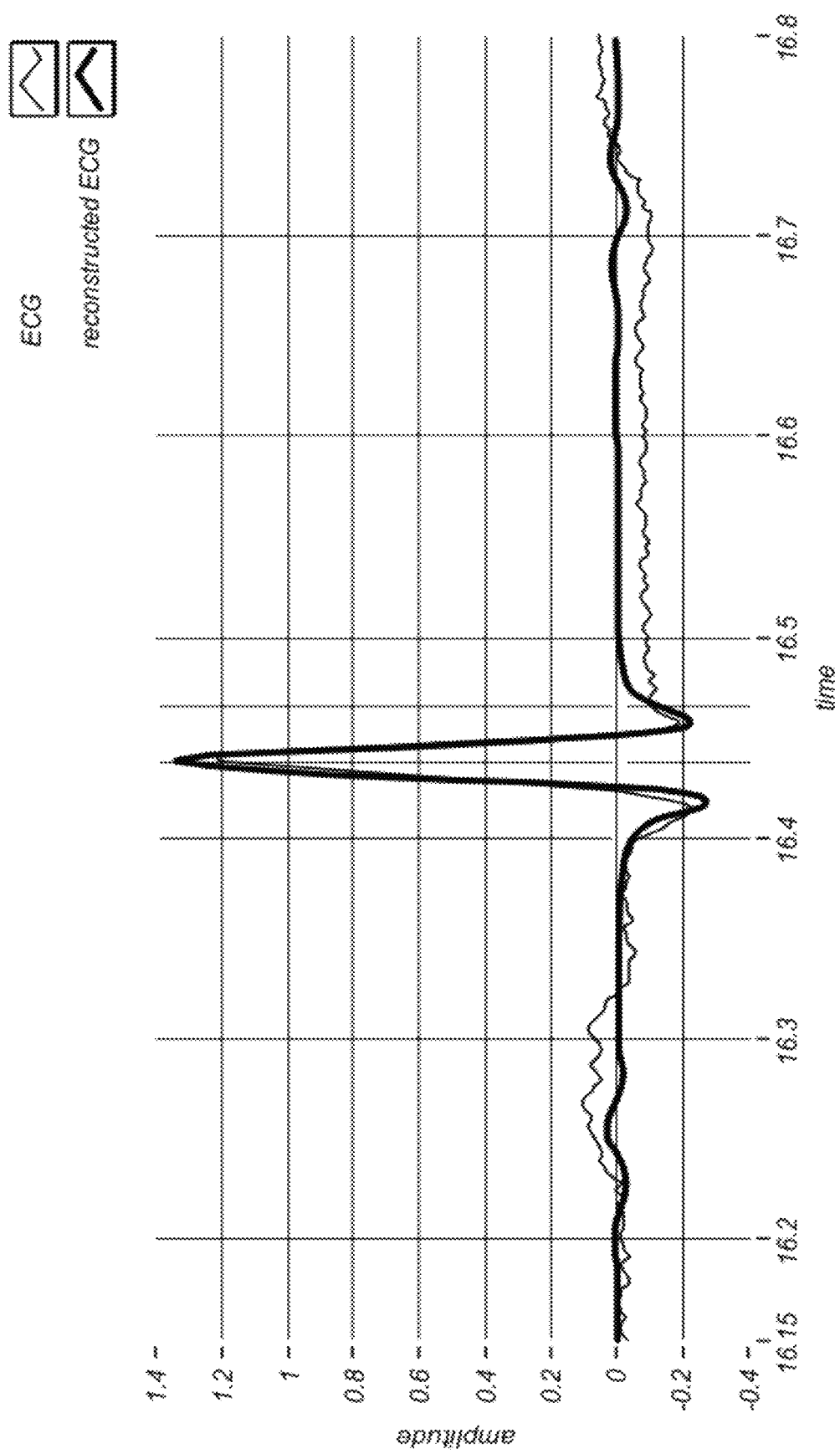
FIG. 9 illustrates one possible realization for display output provided by the method of FIG. 4.

FIG. 9 shows one embodiment of the possible display output. The ECG signal (thin dark line) is captured from record 100 in MIT-BIH Arrhythmia DB. The smooth signal (thick line) is computed based on expression (6). Observe that the estimated onset, center and offset times of the QRS complex are indicated with vertical lines.

Figure 10:
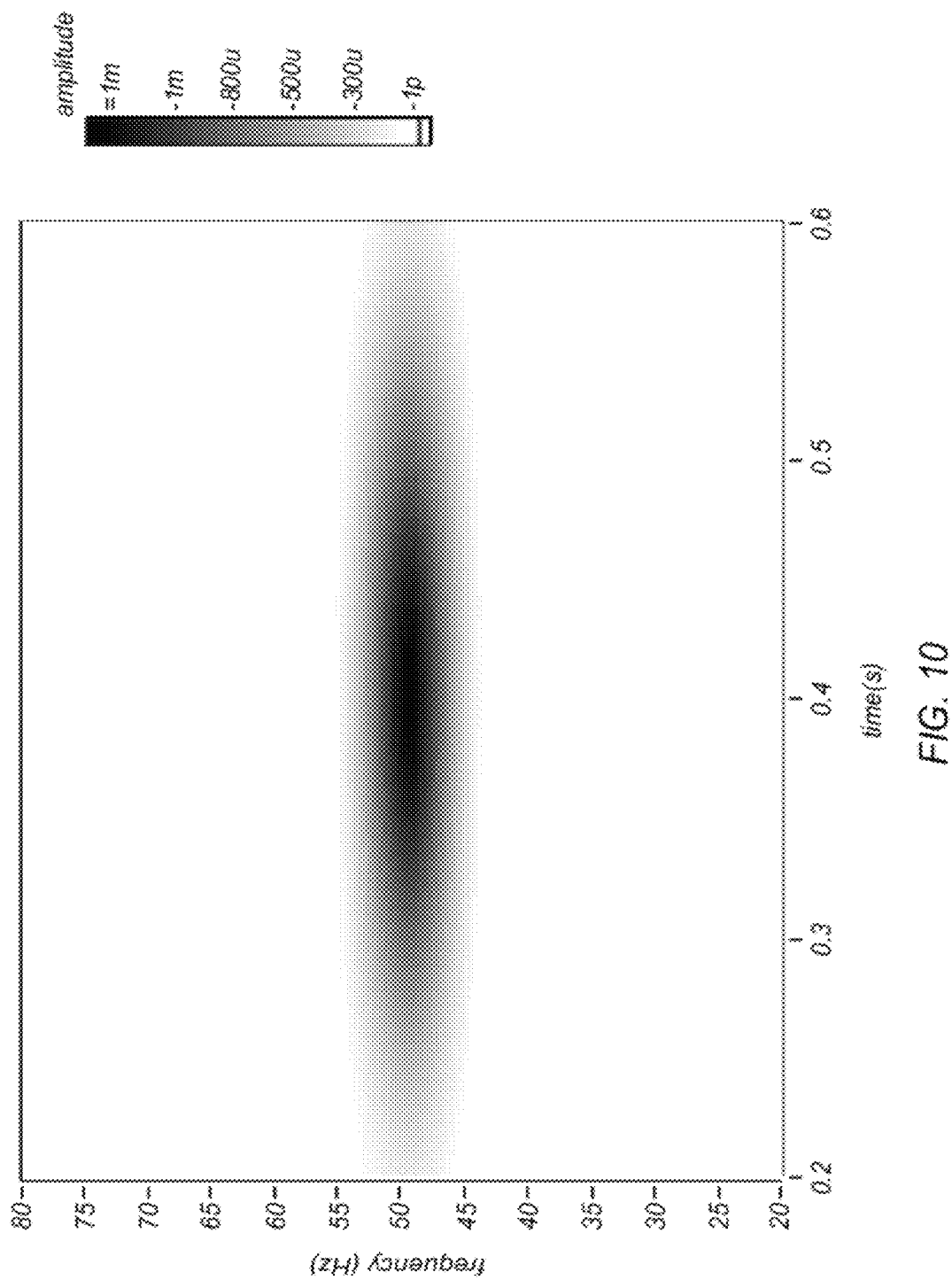
FIG. 10 illustrates the spectrogram amplitude for a Gaussian-modulated sinusoid centered at (0.4 sec, 50 Hz).

FIG. 10 shows the spectrogram amplitude for a frequency-modulated Gaussian function whose center is at (0.4 sec, 50 Hz). Gray scale is used to indicate amplitude. Thus, the amplitude has a peak at (0.4 sec, 50 Hz).

Figure 11:
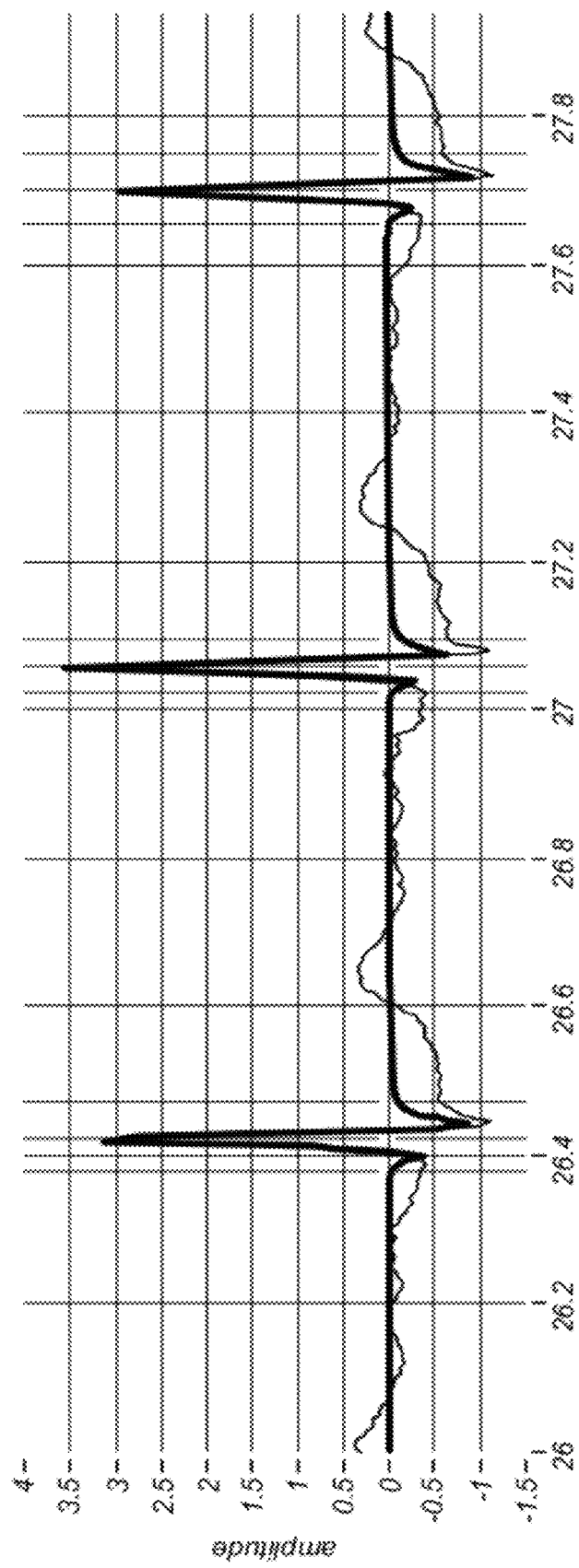
FIG. 11 illustrates one possible realization for display output provided by the method of FIG. 5.

FIG. 11 shown another embodiment of the possible display output. The ECG signal (thin dark line) is a captured ECG signal. The smoothed signal (thick line) is computed using the parameters of the estimated QRS complexes. Again, observe that the onset, center and offset times of the estimated QRS complexes are indicated with vertical lines.

Although the embodiments above have been described in considerable detail, numerous variations and modifications will become apparent to those skilled in the art once the above disclosure is fully appreciated. It is intended that the following claims be interpreted to embrace all such variations and modifications.

What is claimed is:

1. A non-transitory computer-readable memory medium storing program instructions, wherein the program instructions, if executed by a computer system, cause the computer system to:

perform a multiscale short-time Fourier transform (STFT) on a set of samples to obtain a transform array that is parameterized by window width, window displacement $\tau$ and frequency $\omega$, wherein the set of samples represents a portion of an electrocardiogram (ECG) signal, wherein the portion of the ECG signal includes a number of waveform features;

operate on the transform array to determine a plurality of peaks in the transform array, wherein said operating includes determining, for each of the plurality of peaks, a window width value, a window displacement value, a frequency value and a power value;

generate, for each of the plurality of peaks, a refined window width value and a refined window displacement value, by:

computing an inner product between the set of samples and each of a plurality of functions, wherein the plurality of functions are windowed sinusoids (a) having a common frequency equal to the frequency value of the peak, (b) being centered at times that are in a neighborhood of the window displacement value of the peak, and (c) having a common width that is based on the width value of the peak; and solving a linear system Av=c for the unknown vector v, wherein the vector c is determined by the inner products, wherein the matrix A is determined by said times that are in the neighborhood of the window displacement value of the peak.

2. The memory medium of claim 1, wherein the program instructions, if executed by the computer system, further cause the computer system to:

identify a first of the peaks as corresponding to a QRS complex based on a determination that the power value of the first peak exceeds a threshold value and that the refined window displacement value for the first peak satisfies one or more time constraints;

compute a QRS onset time and/or a QRS offset time based on the refined window displacement value and the refined window width of the first peak; and display the QRS onset time and/or the QRS offset time via a display device.

3. The memory medium of claim 2, wherein the program instructions, if executed by the computer system, further cause the computer system to:

repeat said performing, said operating and said generating for a series of sets of samples of the ECG signal.

4. The memory medium of claim 2, wherein the threshold value is an adaptive threshold that changes over time.

5. The memory medium of claim 2, wherein the one or more time constraints include a time constraint on the refined window displacement value of the first peak relative to a time of a previously identified feature in the ECG signal.

6. The memory medium of claim 1, wherein the program instructions, if executed by the computer system, further cause the computer system to:

compute, for each peak $P_j$ of the plurality of peaks, a windowed sinusoid function $h_j$ that is determined by the refined window width value of the peak $P_j$, the refined window displacement value of the peak $P_j$, and the frequency value of the peak $P_j$;

generate a linear combination of the windowed sinusoid functions $h_j$; and display the real part of the linear combination via a display device.

7. The memory medium of claim 1, wherein the ECG signal is a human ECG signal, wherein the waveform features include one or more of the following: a P wave, a QRS complex and a T wave.

8. The memory medium of claim 1, wherein the windowed sinusoids are Gaussian-modulated complex exponentials.

9. The memory medium of claim 1, wherein said operating on the transform array includes searching for the $N_P$ peaks of largest absolute value in the transform array, wherein $N_P$ is a positive integer.

10. The memory medium of claim 9, wherein said searching is restricted to a band of frequencies that is smaller than the frequency range of the multiscale STFT.

11. A non-transitory computer-readable memory medium storing program instructions, wherein the program instructions, if executed by a computer system, cause the computer system to:

receive samples of a portion of an electrocardiogram (ECG) signal, wherein said portion of the ECG signal contains a waveform feature;

operate on the samples to compute a plurality of short-time Fourier transforms (STFT), wherein each of the STFTs is computed using a different value of window width, wherein each of the STFTs is a function of window displacement time $\tau$ and frequency $\omega$;

search the plurality of STFTs to determine an initial set of parameters values that characterize the waveform feature, wherein the initial set of parameter values includes a first window displacement time $\tau_0$, a first frequency $\omega_0$ and a first window width $\sigma_0$;

compute an inner product of the samples with each of a first function, a second function and a third function to obtain respectively a first complex value, a second complex value and a third complex value, wherein the first, second and third functions are windowed sinusoids (a) having a common frequency equal to the first frequency $\omega_0$, (b) being centered at times that are in a neighborhood of the first window displacement time $\tau_0$, and (c) having a common width that is based on the first window width $\sigma_0$;

compute a time of the waveform feature and a duration of the waveform feature based on the first, second and third complex values and based on said times in the neighborhood of the first window displacement time $\tau_0$; and store the waveform feature time and the waveform feature duration in a memory.

12. The memory medium of claim 11, wherein the program instructions, if executed by the computer system, further cause the computer system to:

display the waveform feature time or a visual indication of the waveform feature time via a display device.

13. The memory medium of claim 11, wherein the waveform feature is a QRS complex, wherein the program instructions, if executed by the computer system, further cause the computer system to:

compute an onset time and/or an offset time of the QRS complex based on the waveform feature time and the waveform feature duration.

14. The memory medium of claim 11, wherein the waveform feature is a QRS complex, a T wave or a P wave.

15. The memory medium of claim 11, wherein the plurality of STFTs are computed using Gaussian windows.

16. The memory medium of claim 11, wherein the windowed sinusoids are Gaussian-modulated complex exponentials.

17. The memory medium of claim 11, wherein said searching includes searching for a local maximum or global maximum of absolute value in the STFTs.

18. The memory medium of claim 11, wherein the ECG signal is a human ECG signal, wherein said searching is restricted to frequencies in the interval from 10 Hz to 25 Hz.

19. The memory medium of claim 11, wherein said computing the waveform feature time and the waveform feature duration includes solving a linear system Av=c for the unknown vector v, wherein the matrix A is determined by said times in the neighborhood of the first window displacement time $\tau_0$, wherein the vector c is determined by the first, second and third complex values.

20. The memory medium of claim 19, wherein the vector c is determined by the expression:

$$c = [\ln|z_0|/|z_{-1}|, \ln|z_0|/|z_{+1}|]^T,$$

wherein $z_0$, $z_{-1}$ and $z_{+1}$ are the first, second and third complex values, respectively.

21. The memory medium of claim 11, wherein the times that are in the neighborhood of the first window displacement time $\tau_0$ include $\tau_0$, $\tau_0 \Delta\tau$ and $\tau_0 - \Delta\tau$, where $\Delta\tau$ is a positive real number.

22. A method comprising:

a computer system receiving samples of a portion of an electrocardiogram (ECG) signal, wherein said portion of the ECG signal contains a waveform feature;

the computer system operating on the samples to compute a plurality of short-time Fourier transforms (STFT), wherein each of the STFTs is computed using a different value of window width, wherein each of the STFTs is a function of window displacement time $\tau$ and frequency $\omega$;

the computer system searching the plurality of STFTs to determine an initial set of parameters values that characterize the waveform feature, wherein the initial set of parameter values includes a first window displacement time $\tau_0$, a first frequency $\omega_0$ and a first window width $\sigma_0$;

the computer system computing an inner product of the samples with each of a first function, a second function and a third function to obtain respectively a first complex value, a second complex value and a third complex value, wherein the first, second and third functions are windowed sinusoids (a) having a common frequency equal to the first frequency $\omega_0$, (b) being centered at times that are in a neighborhood of the first window displacement time $\tau_0$, and (c) having a common width that is based on the first window width $\sigma_0$;

the computer system computing a time of the waveform feature and a duration of the waveform feature based on the first, second and third complex values and based on said times in the neighborhood of the first window displacement time $\tau_0$; and the computer system storing the waveform feature time and the waveform feature duration in a memory.

* * * * *